US00PP27090P3

(12) United States Plant Patent
Spencer

(10) Patent No.: US PP27,090 P3
(45) Date of Patent: Aug. 23, 2016

(54) ***NEPETA GRANDIFLORA* PLANT NAMED 'SUMMER MAGIC'**

(50) Latin Name: *Nepeta grandiflora*
Varietal Denomination: SUMMER MAGIC

(71) Applicant: Malcolm Joseph Robert Spencer, Bognor Regis (GB)

(72) Inventor: Malcolm Joseph Robert Spencer, Bognor Regis (GB)

( * ) Notice: Subject to any disclaimer, the term of this patent is extended or adjusted under 35 U.S.C. 154(b) by 150 days.

(21) Appl. No.: 14/120,623

(22) Filed: Jun. 9, 2014

(65) Prior Publication Data

US 2015/0230380 P1 Aug. 13, 2015

(30) Foreign Application Priority Data

Feb. 7, 2014 (QZ) ..... PBR 2014/0310

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith Robinson
(74) *Attorney, Agent, or Firm* — Cassandra Bright

(57) ABSTRACT

A new and distinct *Nepeta* cultivar named 'SUMMER MAGIC' is disclosed, characterized by plants with a compact, bushy habit and improved resistance to wind and rain damage. Flower stems have improved branch structure and plants produce a large quantity of flowers. The new cultivar is a *Nepeta*, suitable for ornamental garden purposes.

3 Drawing Sheets

Latin name of the genus and species: *Nepeta grandiflora.*
Variety denomination: 'SUMMER MAGIC'.

BACKGROUND OF THE INVENTION

The new cultivar is a product of chance discovery by the inventor. This new variety, hereinafter referred to as 'SUMMER MAGIC', was discovered as a chance seedling by the inventor, Malcolm Spencer. The seed parent is believed to be *Nepeta grandiflora* 'Bramdean', unpatented and the pollen parent undetermined. This interesting new variety was discovered in the inventor's garden during June 2010 as an individual seedling plant. The plant was discovered in West Sussex, England.

After identifying the new variety as a potentially interesting selection, the inventor first propagated 'SUMMER MAGIC' by vegetative terminal stem cuttings during July of 2010, at his home in West Sussex, England. The inventor continued controlled testing and propagation, assessing stability of the unique characteristics of this variety. Subsequently, several generations have been reproduced and have shown that the unique features of this cultivar are stable and reproduced true to type.

SUMMARY OF THE INVENTION

The cultivar 'SUMMER MAGIC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SUMMER MAGIC'. These characteristics in combination distinguish 'SUMMER MAGIC' as a new and distinct *Nepeta* cultivar:

1. Compact bushy habit
2. Improved branch structure on flower stems
3. Improved plant sturdiness; better resistance to wind/rain damage
4. Distinctive strong flower color
5. Large quantity of flowers

COMPARISON TO PARENT VARIETY

'SUMMER MAGIC' is similar in most horticultural characteristics to the presumed seed parent variety *Nepeta grandiflora* 'Bramdean'. Plants of the new cultivar 'SUMMER MAGIC' however, differ in the following:

1. The new variety is shorter.
2. The new variety produces more branches.
3. The new variety has improved resistance to weather damage—parent variety is often broken open by summer storms.

COMMERCIAL COMPARISON

'SUMMER MAGIC' can be compared to the well known commercial variety *Nepeta faassenii* 'Six Hills Giant', unpatented. Plants of the new cultivar 'SUMMER MAGIC' are similar to plants of 'Six Hills Giant' in most horticultural characteristics. Plants of the new cultivar 'SUMMER MAGIC' however, differ in the following characteristics:

1. The new variety is much shorter.
2. The new variety has significantly improved branching on flower stems.
3. The new variety has improved resistance to weather damage.
4. Pinching requirements and or/growth regulator use are eliminated are reduced to produce plants for garden center sales.

'SUMMER MAGIC' can be compared to the known commercial variety *Nepeta racemosa* 'Little Titch', unpatented.

Plants of the new cultivar 'SUMMER MAGIC' are similar to plants of 'Little Titch' in most horticultural characteristics. Plants of the new cultivar 'SUMMER MAGIC' however, differ in the following characteristics:

1. The new variety produces longer flower spikes.
2. The new variety produces more flowers per stem, and more flowering stems per plant.
3. The new variety has improved resistance to weather damage.
4. The new variety produces more branches per plant.

BRIEF DESCRIPTION OF THE PHOTOGRAPHS

The accompanying photograph in FIG. 1 illustrates in full color a typical plant of 'SUMMER MAGIC' grown outdoors in West Sussex, England. The plant is approximately 1 year old, and is shown in a 2 liter container.

Figure 1:
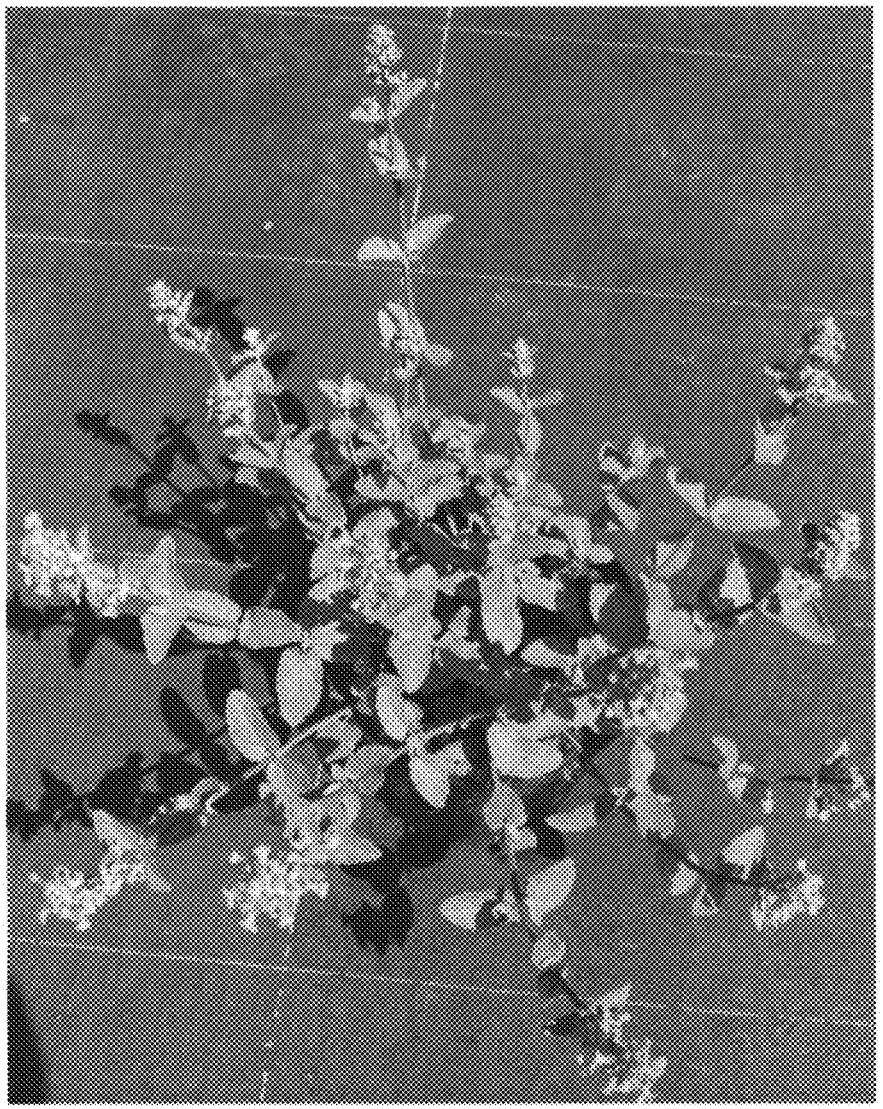
Figure 2:
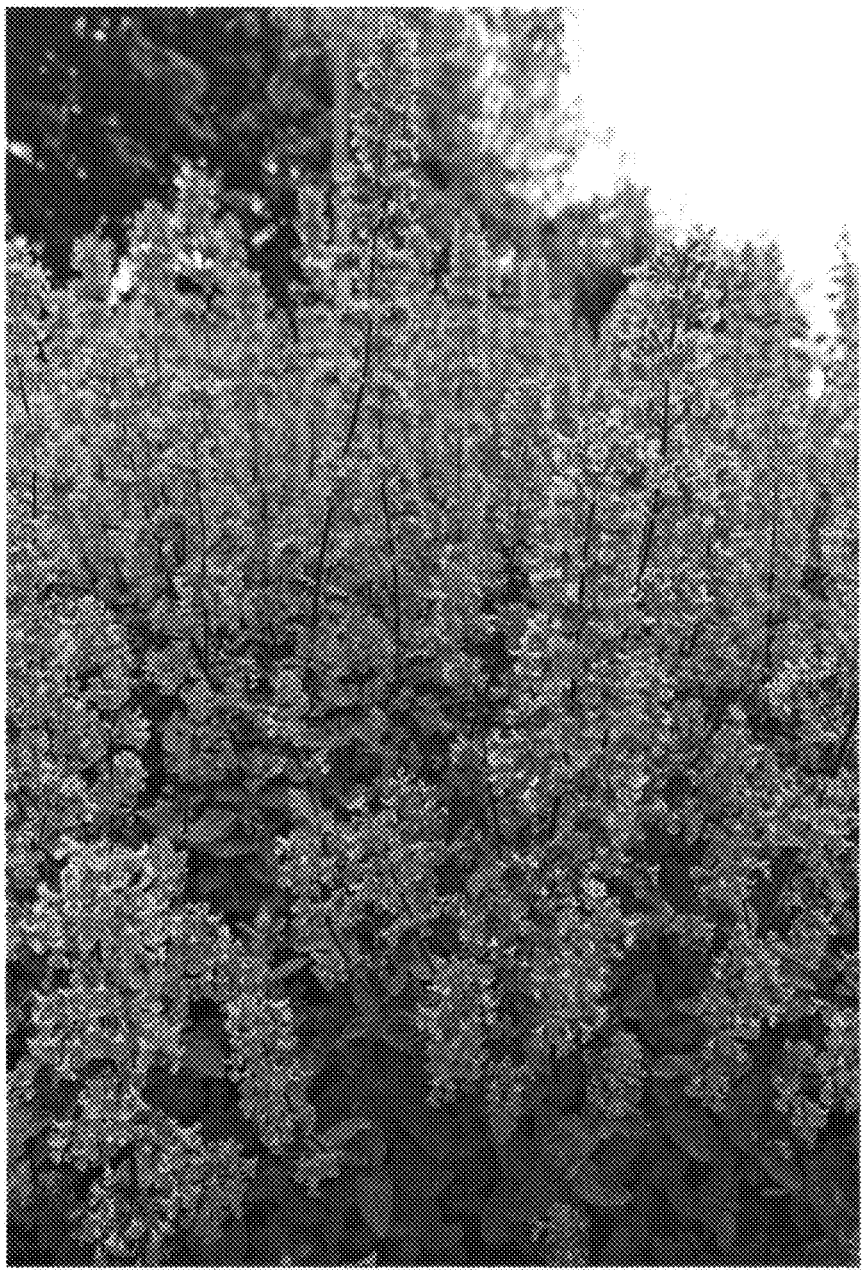
FIG. 2 shows a close up of several flowering spikes.
Figure 3:
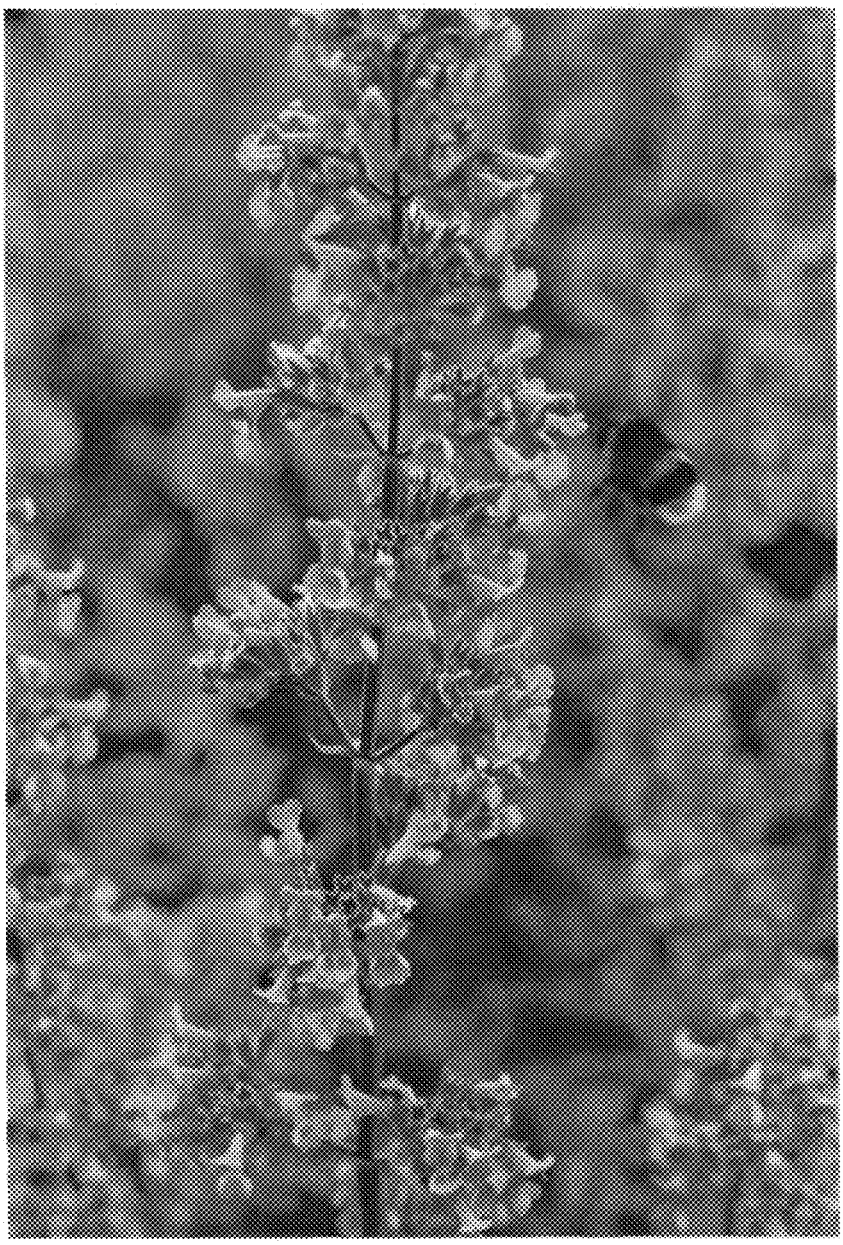
FIG. 3 illustrates in close up perspective a typical flowering spike.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SUMMER MAGIC' plants grown outdoors in West Sussex, England. Plants are approximately 1 year old, in a 2 liter nursery container. Measurements and numerical values represent averages of typical plant types.

Botanical classification: *Nepeta grandiflora* 'SUMMER MAGIC'.

PROPAGATION

Time to initiate roots: About 5 days at approximately 16° C.
Time to produce a rooted cutting: About 14 days at 16° C.
Typical propagation method: Vegetative cuttings.
Root description: Fine, fibrous young roots, dense.

PLANT

Overall plant shape or growth habit: Decumbent, clump forming perennial.
Plant spread: Approximately 50 cm.
Plant height: Approximately 60 cm.
Growth rate: Medium to strong vigor.
Length of primary lateral branches: Approximately 35 cm.
Diameter of lateral branches: Approximately 0.55 cm.
Quantity of lateral branches: About 12.
*Color*.—Near RHS Yellow-Green 144B.
*Texture*.—Pubescent.
Internode length: Approximately 8 cm.
Age of plant described: Approximately 1 year from a rooted cutting.

FOLIAGE

Leaf:
*Arrangement*.—Opposite.
*Quantity*.—Approximately 14 per main branch.
*Average length*.—Approximately 4.5 cm.
*Average width*.—Approximately 2.8 cm.
*Shape of blade*.—Ovate.
*Apex*.—Obtuse.
*Base*.—Cordate.
*Attachment*.—Petiolate.
*Margin*.—Crenulate.
*Texture of top surface*.—Rugose, pubescent.
*Texture of bottom surface*.—Rugose, pubescent.
*Foliage scent*.—Strongly aromatic, typical fragrance for the species.
*Color*.—Young foliage upper side: Near RHS Green N138B. Young foliage under side: Near RHS Green N138C. Mature foliage upper side: Near RHS between Green 137B and N138B. Mature foliage under side: Near RHS Green N138C.
*Venation*.—Type: pinnate. Venation color upper side: Near RHS Green N138A. Venation color under side: Near RHS Yellow-Green 147D.
*Petiole*.—Average Length: Approximately 0.3 cm. Diameter: Approximately 0.2 cm. Color: Near RHS Green 138B. Texture: Pubescent.

FLOWER

Natural flowering season: May to October (at the breeder's location, West Sussex, England).
Inflorescence type and habit: Terminal verticillasters.
Flower longevity on plant: 1 to 2 days.
Quantity of flowers: About 45 blooming spikes per plant. About 180 blooming flowers per spike.
Inflorescence size:
*Diameter*.—Approximately 4.1 cm.
*Height*.—Approximately 45 cm.
*Flowers and buds per inflorescence*.—9-12 opposite pairs of cymes per verticillaster; 6-18 flowers per cyme.
Pedicel:
*Length*.—0.8 cm.
*Diameter*.—0.1 cm.
*Texture*.—Pubescent.
*Color*.—Between RHS Greyed-Purple N187A and Purple N77A.
*Orientation*.—Approximately 45 degrees angle of emergence, straight to occasionally curved.
*Strength*.—Strong and stiff.
Peduncle:
*Length*.—Average range 10 to 20 cm.
*Diameter*.—0.6 cm.
*Texture*.—Pubescent.
*Color*.—Near RHS Yellow-green, flushed Purple N77B.
*Orientation*.—Approximately 0 to 15 degrees angle of emergence, straight to occasionally curved.
*Strength*.—Strong and stiff.
Individual flowers:
*Petal arrangement*.—The corolla is sympetalous and typically bilabiate with 2 small, highly fused lobes forming an upper lip and 3 larger highly fused lobes forming a lower lip.
Size:
*Diameter*.—Approximately 0.7 cm.
*Length*.—Approximately 1.2 cm.
*Persistence*.—Non-persistent.
*Fragrance*.—None noted.

Petals:

*Margin*.—Crenate at lower and upper lips.

*Tip shape*.—Upper lip: slightly reflexed. Lower lip: slightly cupped.

*Length*.—Upper lip: 0.4 cm. Lower lip: 0.6 cm. Tube: 0.5 cm.

*Width*.—Upper lip: 0.5 cm. Lower lip: 0.6 cm. Tube: 0.2 cm.

*Texture*.—Upper lip: pubescent on outer surface, glabrous on inner surface. Lower lip: pubescent on outer surface, glabrous on inner surface. Tube: pubescent.

Color:

*Upper lip*.—When opening: Inner surface: Near RHS Violet N88B. Outer surface: Near RHS Violet-Blue 90C. Fully opened: Inner surface: Near RHS Violet N88A. Outer surface: Between RHS Violet N87B and N87C. Fading: Inner surface: Near RHS Violet N88A. Outer surface: Near RHS Violet N87C.

Color:

*Lower lip*.—When opening: Inner surface: Near RHS Violet N88B. Outer surface: Near RHS Violet-Blue 90C. Fully opened: Inner surface: Near RHS Violet-Blue 93B. Outer surface: Near RHS Violet-Blue 94B. Fading: Inner surface: Near RHS Violet-Blue 95B. Outer surface: Near RHS Violet-Blue 95C.

Color:

*Tube*.—When opening: Inner surface: Near RHS Violet-Blue 92A. Outer surface: Near RHS Violet-Blue 90D. Fully opened: Inner surface: Near RHS Violet-Blue 91A. Outer surface: Between RHS Violet-Blue 90D and 91A. Fading: Inner surface: Near RHS Violet-Blue 91B. Outer surface: Between RHS Violet-Blue 91A and 91B.

Bud:

*Shape*.—Olong.

*Length*.—0.6 cm.

*Diameter*.—0.3 cm.

*Color*.—Between RHS Violet-Blue 91A and 92A.

Sepals:

*Shape*.—Tubular.

*Quantity per flower*.—5, lobed.

*Length*.—Approximately 0.4 cm.

*Width*.—Approximately 0.3 cm.

*Margin*.—Lobes narrow, tips acuminate.

*Apex*.—Acute.

*Base*.—Fused.

*Texture*.—Pubescent, upper and lower surfaces.

*Color, upper and lower surfaces*.—Between Green 142B and 142C at base, changing to Purple N79B at the tips of the lobes.

REPRODUCTIVE ORGANS

Stamens:

*Number*.—4.

*Filament length*.—Approximately 0.5 cm.

*Filament color*.—Near RHS Purple 76C.

Anthers:

*Shape*.—Globular.

*Length*.—Approximately less than 0.1 mm.

*Diameter*.—Less than 0.1 mm.

*Color*.—Near RHS Purple N77A.

*Pollen*.—Color: Near RHS White N155A. Quantity: sparse.

Pistil:

*Number*.—1.

*Length*.—Approximately 1.1 cm.

*Style*.—Length: Approximately 0.9 cm. Diameter: Approximately 1 mm. Color: Near RHS White N155A at base, changing to Violet-Blue 91A towards tip.

*Stigma*.—Shape: cleft. Length: Approximately 1 mm. Color: Near RHS Violet N88A. Ovary color: Near RHS Green 142B.

OTHER CHARACTERISTICS

Disease and pest resistance: Not observed to be susceptible nor resistant to normal diseases and pests of *Nepeta grandiflora*.

Temperature tolerance: USDA Zone 4 through 9.

Fruit/seed production: Not observed to date.

What is claimed is:

1. A new and distinct cultivar of *Nepeta* plant named 'SUMMER MAGIC' as herein illustrated and described.

* * * * *